United States Patent [19]
Podzuweit

[11] Patent Number: 6,066,649
[45] Date of Patent: *May 23, 2000

[54] DRUG FOR CARDIOVASCULAR DISEASES

[75] Inventor: Thomas Podzuweit, Liebigstrasse 10, D-61231, Bad Nauheim, Germany

[73] Assignee: Thomas Podzuweit, Bad Nauheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/313,239

[22] PCT Filed: Apr. 2, 1993

[86] PCT No.: PCT/EP93/00827

§ 371 Date: Feb. 28, 1995

§ 102(e) Date: Feb. 28, 1995

[87] PCT Pub. No.: WO93/19742

PCT Pub. Date: Oct. 14, 1993

[30] Foreign Application Priority Data

Apr. 3, 1992 [DE] Germany .................. P 42 11 239

[51] Int. Cl.⁷ .................................................. A61K 31/44
[52] U.S. Cl. ................... 514/303; 514/258; 514/465; 514/704; 514/742; 514/929
[58] Field of Search .................... 514/258, 303, 514/465, 929, 740, 742

[56] References Cited

U.S. PATENT DOCUMENTS 3,987,160 10/1976 Broughton et al. .................. 424/45

OTHER PUBLICATIONS

Database MEDLINE on STN Koke et al, "Inhibitors of adenosine catabolism improve recovery of dog myocardium after ischemia", Molecular and cellular Biochemistry, 86(2) 107–13, Apr. 11, 1989.

Database Chemical Abstracts on STN, Wu et al, "Contractility, ATP, and creatine phosphate during myocardial ischemia and reperfusion . . . ", Cytobios, 50(200), 7–12, Jan. 1987.

MEDLINE Abstract, AN 76138485, Epstein et al, Mar., 1976.

MEDLINE Abstract, AN 91005785, Zhu, Apr., 1990.

Trapani et al, "Hemodynamic Basis for the Depressor Activity of Zaprinast, a Selective cGMP Phosphodiesterase Inhibitor", J. Pharm. & Exp. Therap., vol. 28, No. 1, pp. 269–274, Apr. 09, 1991.

Harris et al, "Phosphodiesterase inhibition and the potentation by zaprinast . . . ", J. Phar.&Exp. Therap., vol. 249, No. 2, pp. 349–400, Jan. 23, 1989.

*Primary Examiner*—Keith D. MacMillan
*Attorney, Agent, or Firm*—Sughrue, Mion, Zinn, Macpeak & Seas, PLLC

[57] ABSTRACT

The invention relates to a drug, which contains one or more inhibitors for the cGMP-stimulated phosphodiesterase (PDE II) together with conventional substrates and/or diluents. Preferably the drug contains erythro-9-(2-hydroxy-3-nonyl)-adenine or 2-o-propoxyphenyl-8-azapurine-6-one, optionally together with one or more activators of guanyl cyclase. The invention also relates to the application of inhibitors of cGMP-stimulated phosphodiesterase (PDE II) for the control and prophylaxis of cardiovascular diseases and for the manufacture of drugs for cardiovascular diseases. Preferably erythro-9-(2-hydroxy-3-nonyl)-adenine or 2-o-propoxyphenyl-8-azapurine-6-one is used, optionally together with one or more activators of guanyl cyclase.

7 Claims, 1 Drawing Sheet

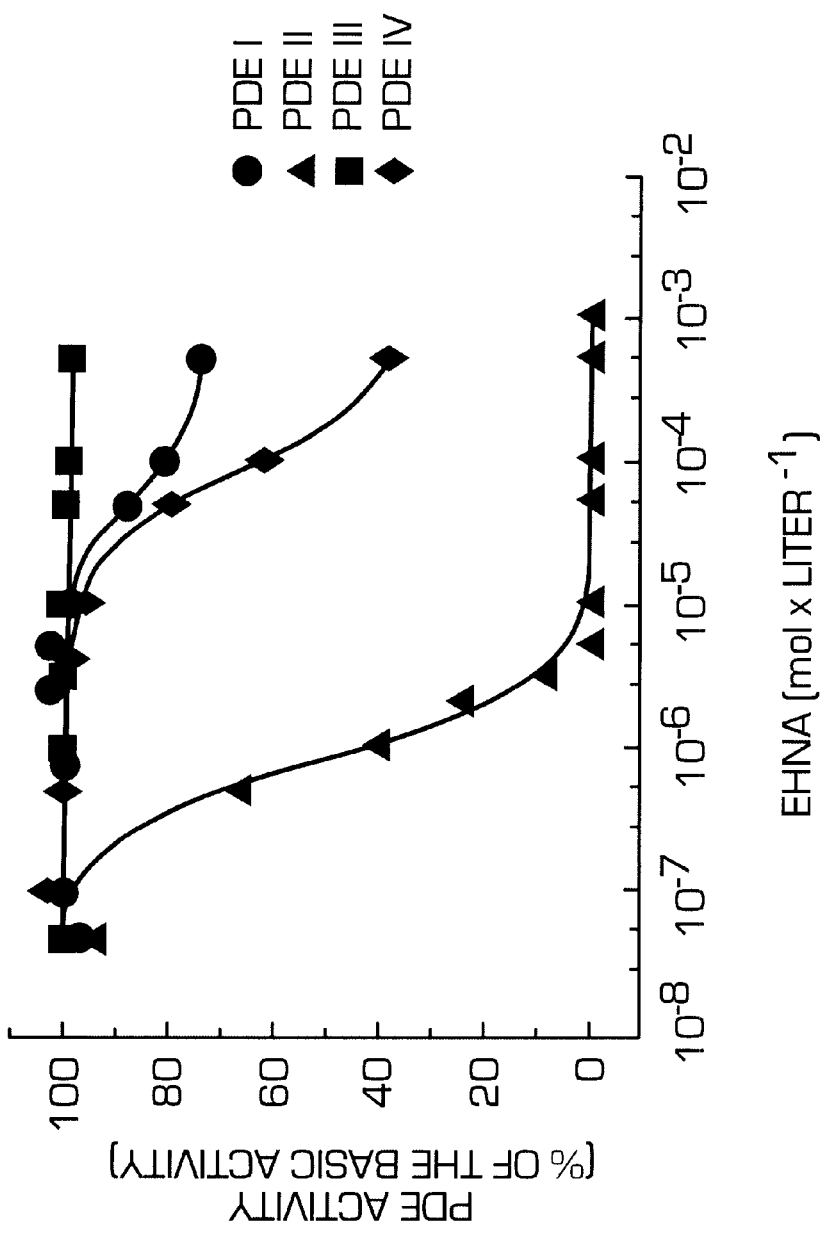

DRUG FOR CARDIOVASCULAR DISEASES

This application is a 371 of PCT/EP93/00827, filed Apr. 2, 1993.

The invention relates to a drug for cardiovascular diseases, in particular dysrhythmia, cardiac insufficiency, myocardial ischemia, angina pectoris and high blood pressure (hypertension), which contains a specific inhibitor, and the application of the specific inhibitor.

Cardiovascular diseases belong to the main reasons for death in the industrialized countries. If the heart is no longer capable of producing an output corresponding to the requirements, i.e. if it no longer has the strength to pump the amount of blood, corresponding to the venous supply, into the circulatory periphery, one talks about a cardiac insufficiency. In so doing, one distinguishes, according to the section of the heart that is affected, between a right ventricular insufficiency, a left ventricular insufficiency and a bilateral insufficiency (global insufficiency), depending on the degree of severity an insufficiency at rest or exercise. A cardiac insufficiency can have mechanical or biochemical causes. A mechanically induced cardiac insufficiency is possible due to long-term overloading of the myocardium as a consequence of increased resistance in the general or lesser circulatory system (e.g. for chronic lung diseases, mitral or aortic stenosis, hypertension), due to the lack of heart muscle fibers associated with myocarditis or heart infarction, dysrhythmia (tachycardia, bradycardia) or due to an obstruction of the heart activity owing to constrictive pericarditis or pericardial tamponade. A biochemically induced cardiac insufficiency occurs when there is a lack of substrate in the heart muscle following inadequate circulation of the blood flow (coronary insufficiency) or disturbed diffusion from the capillaries into the muscle fibers (e.g. with myocarditis) and due to insufficient conversion of chemical energy into mechanical energy as a consequence of a disordered electrolyte or metabolism (shift in K/Ca quotient, lack of vitamin $B_1$, diabetes mellitus).

The primary goal of drug therapy for cardiac insufficiency is to economize the work of the heart and to raise the contraction strength of the heart muscle fibers.

In so doing, cardiac irregularities, from which young persons can suffer, but which are especially typical in older persons, deserve special attention. The pathological changes underlying cardiac irregularities are based on a disturbance in the formation of excitation and/or a disturbance in the conduction. At the same time the heart rate can be too high (tachycardia), too low (bradycardia) or irregular (arrhythmia).

Ventricular fibrillation is often the cause of sudden cardiac death. In the genesis of such arrhythmias biochemical factors are becoming increasingly more important. However, the exact origin of ventricular fibrillation remains speculative; and to date there still does not exist an effective therapy with drugs. According to one hypothesis, the local concentration of calcium ions released from the heart is associated with the start of arrhythmias and ventricular fibrillation, but the loss of calcium ions and the ventricular fibrillation is sometimes unrelated. It has been proposed that cyclic adenosine monophosphate, the second messenger of cateocholamine activity, is related to the start of ventricular fibrillation.

Therefore, physiological mechanisms, which regulate the synthesis or decomposition of cAMP in ischemic cells, should be significant for the development of a drug for ventricular fibrillation (T. Podzuweit, W. F. Lubbe and L. H. Opie, Lancet i, 341-342, 1976).

In the case of pigs it has been found that early ventricular arrhythmias and ventricular fibrillation, induced by occlusions of the coronary arteries, correlate to increased levels of myocardial cAMP and adenosine. In addition, a relation between the cAMP and adenosine content of ischemic myocardium and the frequency of reperfusive ventricular fibrillation has been proven. Ventricular fibrillation, induced by the proximal occlusion of the Ramus inter ventricularis anterior (Riva) of the left coronary artery, was not hindered by pretreatment of pigs with atenolol (0.2 to 1.0 mg/kg i.v).

Cyclic nucleotides act as second messengers in the hormonal regulation of cell metabolism. Different hormones activate via an enzyme system that is localized in the membrane of receptor cells the adenyl cyclase, which converts ATP into cAMP. The cAMP activates one or more protein kinases of this cell, which in turn catalyze the ATP-dependent phosphorylation of important key enzymes of the intermediary metabolism and the phosphorylation of membrane-based proteins. For the genesis of arrhythmias it is important that the activity of specific calcium channels is controlled through a cAMP-dependent phosphorylation. The phosphorylation of $Ca^{2+}$ channels (or a protein closely associated with said $Ca^{2+}$ channels) through cAMP-dependent protein kinases results in an increase in the probability that these $Ca^{2+}$ channels will open. The effect provoked by cAMP is eliminated by the decomposition of cAMP, which is in turn controlled, through a specific phosphodiesterase. Analogously cGMP is synthesized by the enzyme guanyl cyclase and decomposed by phosphodiesterases.

Four soluble phosphodiesterases were isolated from extracts of the human papillary muscle using anion exchange chromatography. These enzyme activities were called PDE I to IV according to their sequence of elution with an increasing salt gradient (NaOAc or NaCl (T. Podzuweit et al., J. Mol. Cell. Cardiol. 23, Supplement V, 1991, Abstract P217).

Even though the primary sequences of more than 15 different cyclic nucleotide phosphodiesterases of mammals are known, to date no inhibitor that distinguishes between members of the same family has been developed (J. A. Beavo and D. H. Reifsnyder, TiPS, Reviews, April 1990, volume 11, pages 150 to 155).

J. Cardiovasc. Pharmacol., 5(6), 1983, 1040–7 describes the effect of adenosine-deaminase inhibitors EHNA and 2'-deoxycoformycin on the functional and biochemical recovery of the heart from an ischemia.

Eur. Pharmacol., 200, 1991, 83–7 describes that the unselective PDE-inhibitor Zaprinast raises the cGMP content of the rat aorta as a function of the-dose.

J. Pharmacol. Exp. Ther., 258 (3), 1991, 972–8 describes the interaction of Zaprinast and activators of soluble guanylate cyclase.

J. Pharmacol. Exp. Ther., 249(2), 1989, 394–400 also describes the interaction of Zaprinast and activators of soluble guanylate cyclase.

The EP-A-0 463 756 describes inhibitors of cGMP phosphodiesterase for the treatment of cardiovascular diseases. They are novel inhibitors that inhibit preferably cGMP phosphodiesterases as opposed to cAMP phosphodiesterases. However, the inhibitors are unselective with respect to the individual cGMP-PDE isoenzymes.

The present invention is based on the problem of providing inhibitors that can inhibit selectively different cyclic nucleotide phosphodiesterase isoenzymes. In particular an inhibitor for the cGMP-stimulated phosphodiesterase (PDE II) is to be made available. According to the invention, a drug shall be made available that is suitable for the treatment of cardiovascular diseases. Furthermore, the use of inhibitors of the cGMP-stimulated phosphodiesterase (PDE II) for the control and prophylaxis of cardiovascular diseases and for the manufacture of drugs for cardiovascular diseases shall be made available. In addition, activators of guanyl cyclase shall be made available, through which the effect of the inhibitors is intensified.

It has been found surprisingly that inhibitors of cGMP-stimulated phosphodiesterase (PDE II) are strong antiarrhythmic agents, whose effect can be intensified through activators of guanyl cyclase. In detail it has been proven that the known adenosine deaminase inhibitor EHNA (erythro-9-(2-hydroxy-3-nonyl)-adenine) and 2-o-propoxyphenyl-8-azapurine-6-one are strong antiarrhythmic agents and selective inhibitors of cGMP-stimulated PDE II. In the past the effects of EHNA were explained via the inhibition of adenosine deaminase. Now the invention shows, first of all, using arrhythimas as an example that the effect of EHNA and 2-o-propoxypheny-8-azapurine-6-one is based on the selective inhibition of cGMP-stimulated PDE II, eventually in interaction with the inhibition of the adenosine deaminase.

The invention relates to the application of erythro-9-(2-hydroxy-3-nonyl)-adenine or 2-o-propoxyphenyl-8-azapurine-6-one as inhibitors of cGMP-stimulated phosphodiesterase (PDE II) for the control and prophylaxis of cardiovascular diseases. Cardiovascular diseases include especially dysrhythmia, cardiac insufficiency, myocardial ischemia, angina pectoris and high blood pressure (hypertension). Furthermore, the invention relates to the application of erythro-9-(2-hydroxy-3-nonyl)-adenine or 2-o-propoxyphenyl-8-azapurine-6-one as inhibitors of cGMP-stimulated phosphodiesterase (PDE II) for the manufacture of drugs for the control and prophylaxis of cardiovascular diseases, especially for dysrhythmia, cardiac insufficiency, myocardial ischemia, angina pectoris and high blood pressure (hypertension), with or without one or more activators of guanyl cyclase.

The invention also relates to erythro-9-(2-hydroxy-3-nonyl)-adenine or 2-o-propoxyphenyl-8-azapurine-6-one as an inhibitor for the cGMP-stimulated phosphodiesterase (PDE II) for use for cardiovascular diseases, in particular for disordered action of the heart, cardiac insufficiency, myocardial ischemia, angina pectoris and high blood pressure (hypertension), with or without one or more activators of guanyl cyclase.

EHNA is commercially available and can be bought, for example, from Sigma Chemie GmbH, Grünwalder Weg 30, 8024 Deisenhofen.

The 2-o-propoxyphenyl-8-azapurine-6-one of the following structural formula

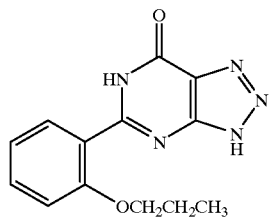

can be manufactured according to the information in the literature (cf. for example B. J. Broughton et al., J. Med. Chem., vol. 18 (II), 1117). The systematic name of this compound reads 1,4-dihydro-5-(2-propoxyphenyl-7H-1,2,3-triazolo[4,5-d]pyrimidine-7-one). The compound is a colorless powder and slightly soluble in water. It dissolves in acetone and ethanol and weakly basic solutions. The compound is stable and has low toxicity. The acute oral $LD_{50}$ for the mouse, rat and rabbit ranges from 1,400 to 2,000 mg/kg per anion.

As the guanyl cyclase activator all such compounds, of which this activity is known, can be used according to the invention. Examples are nitrites, organic nitrates, nitroso compounds and a plurality of other nitrogen oxide-containing substances, including sodium nitroprusside. These compounds are known and are described, for example in Goodman and Gilman's *The Pharmacoloqical Basis of Therapeutics*, 7th edition, 1985, page 798, and in particular on page 806 in the chapter "Drugs used for the treatment of angina: organic nitrates, calcium channel blockers, and β-adrenergic antagonists."

Among the activators of guanyl cyclase, preferably organic nitrates such as nitroglycerin, isosorbide dinitrate, erythrityl tetranitrate and pentaerythritol, tetranitrate, nitrogen oxide-containing vasodilators, the so called nitrovasodilators, and the atrial natriuretic peptide (ANP=ANF) and bradykinin, the EDRF (endothelium derived relaxing factor) are released from the vessel wall. This EDRF is identical to the NO radical, which is released, e.g., from nitroprusside.

According to the invention, the inhibitors alone are administered orally, for example, in the form of tablets, dragées, capsules, solutions, or intraperitoneally, intramuscularly, subcutaneously, intraarticularly or intravenously, for example, by means of injection or infusion. It is especially preferred that the application according to the invention occurs in such a manner that the active agent is released with delay, that is as a depot. The following statements relate to the application according to the invention. The application according to the invention is suitable for cardiovascular diseases, in particular dysrhythmia, cardiac insufficiency, myocardial ischemia, angina pectoris, and high blood pressure (hypertension). The application according to the invention is suitable for suppressing ischemia-induced arrhythmias, (1) via primary antiarrhythmic action, and
(2) in that it has an anti-ischemic effect, i.e. it acts as a vasodilator.

Furthermore, the application according to the invention does not show a too highly positive inotropy and thus takes the strain off the heart. Due to the vasodilating action of the application according to the invention, it is also suitable for treating hypertension and angina pectoris. Essential is the synergistic effect of the organic nitrates and the PDE-II inhibitor. The tachyphylaxis observed with nitrates could be positively influenced through EHNA.

Unit doses can be administered, for example, 1 to 4 times daily. The exact dose depends on the method of administration and the condition to be treated. Naturally it can be necessary to vary the dose routinely depending on the age and the weight of the patient and the severity of the condition to be treated.

For use according to the invention without activators of the guanyl cyclase, EHNA or Zaprinast can be formulated in the well-known manner using one or more pharmaceutically acceptable substrates or diluents. The preparations can be formulated for oral administration or in a manner suitable for administration by means of injection or infusion.

If, according to the invention, a PDE-II inhibitor and an activator of guanyl cyclase are used, the application can be simultaneous, separate or graduated over time. For example, the drug can contain simultaneously a PDE-II inhibitor and an activator of guanyl cyclase. However, it is also possible that the drug contains only the PDE-II inhibitor; and that the activator of the guanyl cyclase can be administered separately, simultaneously or graduated over time. The method by which the inhibitor and the activator of the guanyl cyclase are administered can differ. For example, the inhibitor can be administered subcutaneously or by means of injection or infusion; and the activator of guanyl cyclase can be administered, for example, through inhalation or as a spray. Thus, the inhibitor and the activator of guanyl cyclase can be combined in different ways.

The pharmaceutical preparations for oral administration can exist, for example, in the form of tablets or capsules, which are manufactured according to well-known methods with pharmaceutically acceptable diluents, such as binders (for example, pregelatinized corn starch, polyvinylpyrrolidone or hydroxypropylmethyl cellulose), fillers (for example lactose, saccharose, mannitol, corn starch, microcrystalline cellulose or calcium hydrogen phosphate); lubricants (for example, stearic acid, polyethylene glycol, magnesium stearate, talcum or silicon dioxide); disintegrators (for example potato starch, sodium starch glycolate or sodium carboxymethyl cellulose); or wetting agents (for example sodium lauryl sulfate). The tablets can be coated according to well-known methods. Liquid preparations for oral administration can exist, for example, in the form of aqueous or oily solutions, syrups, elixirs, emulsions or suspensions, or they can exist as dry products for constitution with water or another suitable carrier prior to application. Such liquid preparations can be prepared according to well-known methods with pharmaceutically acceptable additives, such as suspending agents (for example, sorbitol syrup, cellulose derivatives, glucose/sugar syrup, gelatin, aluminum stearate gel or hydrogenated editable fats); emulsifiers (for example lecithin, gum arabic or sorbitan mono-oleate); non-aqueous carriers (for example almond oil, oily esters, ethyl alcohol or fractionated vegetable oils); and preservatives (for example methyl- or propyl-p-hydroxybenzoates or sorbic acid). The liquid preparations can also contain well-known buffers, taste enhancers or aromatics, dyes and sweetners, as necessary.

For parenteral administration the compounds can be formulated for injection, preferably intravenous, intramuscular or subcutaneous injection or infusion. Preparations for injection can exist as a single dose, for example in ampoules, or multiple dose containers with an added preservative. The preparations can exist as suspensions, solutions or emulsions in oily or aqueous carriers and contain formulating agents, such as suspending agents, stabilizers and/or dispersing agents, and/or agents for adjusting the tonicity of the solution.

Methylxanthines have a long history both as cyclic nucleotide phosphodiesterase (PDE) inhibitors and as adenosine receptor antagonists. The lack of selectivity of these compounds suggests a relation between structural domains of the adenosine receptor and the phosphodiesterase isoenzymes. The present data extends the existing similarities to the enzyme adenosine deaminase (adenosine aminohydrolase, EC 3.5.4.4) (ADA), by showing that the synthetic adenosine deaminase inhibitor erythro-9-(2-hydroxy-3-nonyl)-adenine (EHNA) is also a strong and, to the extend that soluble phosphodiesterases are affected, selective inhibitor of the cGMP-stimulated PDE-II isoenzymes from swine and human myocardium. Since soluble and membrane-stable PDE isoenzymes are similar in their properties, it can be expected with certainty that the results obtained with soluble phosphodiesterases also apply to the membrane-stable enzymes.

Materials and Methods

EHNA-HCl was bought from Burroughs-Wellcome Co. (Greenville, N.C., USA). c[8$^{-3}$H]AMP and c[8$^{-3}$H]GMP were bought from Radiochemical Centre (Amersham, UK). Calmodulin originated from Boehringer (Mannheim, FRG) and DEAE sepharose CL-6B and papaverine originated from Sigma (Deisenhofen, FRG). All other chemicals originated from Merck (Darmstadt, FRG) and were at least of reagent purity. Highly purified water was produced with the Milli-Q-Water Purification System (Millipore Corp., Eschborn, FRG). Fresh stock solutions of inhibitors were produced at least daily under reduced light.

Source of Tissue, Extraction and Chromatography

Samples of the left ventricular papillary muscles were obtained with the consent of patient who underwent an exchange of a mitral flap in the Universitäts-Krankenhaus Gießen, FRG. The myocardium samples of pigs (male pigs of the German breed of swine, 25 to 30 kg body weight) were obtained following excision of the hearts under Nembutal anesthesia. The samples were immediately frozen in liquid nitrogen and were then pulverized in a high speed mill and pre-cooled in liquid nitrogen. The frozen tissue powder was sieved through a screen made of stainless steel (−196° C.) (mesh size: 0.315 mm) in an homogenizing buffer (4° C.) (1 ml per 100 mg of powder), comprising (final concentrations): 20 mM of bis-tris, 2 mM of EDTA, 5 mM of 2-mercaptoethanol, 2 mM of benzamidine, 50 $\mu$M of phenylmethylsulfonylfluoride, 50 mM of sodium acetate, pH 6.5. All of the following steps were conducted at 4° C. The homogenate was centrifuged at 48,000 g for 30 minutes. 50 ml of the supernatant were extracted and loaded on a column (20×1.6 cm) of DEAE-sepharose CL-6B, which had been pre-equilibrated with homogenizing buffers. The column was washed with 200 ml of buffer; and the PDE activities were eluted with a linear gradient ranging from 0.05 to 1 M of sodium acetate in buffer (flow time of the gradient: 500 minutes). The flow rate was 1 ml/min. 5 ml fractions were obtained and tested for PDE activity.

Test for PDE Activity and Determination of $IC_{50}$ Values

The PDE activity was measured with an off line liquid scintillation spectrometry using HPLC. The reaction mixture consisted of (final concentrations): 1 $\mu$M c[8$^{-3}$H]AMP or 1 $\mu$M c[8$^{-3}$H]GMP (9.25 GBq/mmol) (approximately 35,000 cpm), 1 $\mu$M cGMP (if existing), 5 mM $MgCl_2$, $5 \times 10^{-7}$M to $10^{-3}$M of inhibitor (if usable) and 20 mM tris-HCl, pH 7.5, in a total volume of 200 $\mu$l. The enzyme activity was measured at 25° C. with 10 minute incubations. The reaction was started with the addition of 50 $\mu$l of enzyme solution and terminated through injection of 20 $\mu$l of 60% perchloric acid. Aliquots of 20 $\mu$l of acidic supernatant were siphoned off and injected into an automated HPLC system (column LiChrospher RP-18e) (250×4 mm; 5 $\mu$m packing).

The radioactive substrates and the products of the PDE reaction were determined quantitatively using a RACK-BETA 1219 liquid scintillation counter (LKB Wallac, Freiburg, FRG). The $IC_{50}$ values (concentrations with 50% inhibition) were determined with 1 $\mu$M cAMP or cGMP using the peak fractions. The data were fitted with four parameters with the aid of the sigmoidal logistic function.

Results

The soluble PDE isoenzymes from swine and human myocardium were severed by means of anion exchange chromatography using DEAE-sepharose CL-6B. The enzyme activities were called PDE I to IV according to the nomenclature of J. A. Beavo and D. H. Reifsnyder. The PDE II activity was stimulated by means of cGMP (1 μM). The enzyme was inhibited as a function of the dose by means of 2-o-propoxyphenyl-8-azapurine-6-one [$IC_{50}$: $8 \times 10^{-6}$M (PDE I), $3 \times 10^{-5}$M (PDE II)].

However, the swine myocardium lacked the $Ca^{2+}$ calmodulin-stimulated soluble PDE I activity. EHNA showed a concentration-dependent inhibition of the cytosolic cGMP-stimulated PDE II isoenzyme from human myocardium ($IC_{50} = 8 \times 10^{-7}$M). Based on the other soluble PDE isoenzymes, the inhibition of the cGMP-stimulated PDE II subtype was selective and highly dependent on the concentration. The inhibition of the PDE isotypes I, III and IV began at a concentration of EHNA, which inhibited-more than 99% of the cGMP-stimulated enzyme. The results that were obtained are illustrated in the attached figure.

The results show that, as the inhibitor of the enzyme, EHNA was more active than the non-selected PDE inhibitor papaverine ($IC_{50} = 2 \times 10^{-4}$M) on a molar basis. It was also found that EHNA inhibited the soluble cGMP-stimulated PDE II from swine myocardium as a function of the dose ($IC_{50} = 2 \times 10^{-6}$M). The inhibition of the other cyclic nucleotide phosphodiesterases from swine myocardium could be ignored ($IC_{50} > 100$ μM).

BRIEF DESCRIPTION OF THE FIGURE

The FIGURE depicts the inhibition of individual cytosolic PDE isoenzymes from human myocardium by means of EHNA.

DISCUSSION

To date four soluble cyclic nucleotide phosphodiesterase isoenzymes from mammal myocardium were severed using anion exchange chromatography. These enzymes could be differentiated according to their regulatory properties, i.e. the activation by means of cGMP or $Ca^{2+}$ calmodulin or the inhibition by means of cGMP or pharmacological inhibitors. Selective inhibitors were available for the $Ca^{2+}$ calmodulin-stimulated PDE I, the cGMP-inhibited PDE III and the Rolipram-sensitive PDE IV. However, to date selective inhibitors of cGMP-stimulated isoenymes were not available. In the present application it is shown, first of all, that the reversible adenosine deaminase inhibitor EHNA is a strong inhibitor of cytosolic PDE II from swine and human myocardium. Based on the other soluble PDE's, the inhibition was selective for the cGMP-stimulated isoenzyme (cf. the FIGURE) with a $IC_{50}$ value of $8 \times 10^{-7}$M (human) or $2 \times 10^{-6}$M (swine). These data show structural similarities between the catalytic and/or regulatory domains of two apparently unrelated enzymes—adenosine deaminase and cGMP-stimulated cyclic nucleotide phosphodiesterase.

Adenosine deaminase catalyzes the deamination of adenosine, 2'-desoxyadenosine and other different cytotoxic adenosine analogs. This enzyme is inhibited competively by means of the synthetic compound erythro-9-(2-hydroxy-3-nonyl)-adenine (EHNA). At EHNA the ribose rest of adenosine is replaced by an aliphatic chain. ADA is inhibited in two stages, during which the goal of 6-$NH_2$ deamination of EHNA is not affected. The initial bonding step is fast and responds to classical competitive inhibition ($K_1 = 2 \times 10^{-7}$M), a state that is probably related to a bonding of the nonyl-side chain to a hydrophobic region in the vicinity of the catalytic point of ADA. Then a subsequent rearrangement of either the inhibitor or the enzyme follows, resulting in a fixed enzyme-inhibitor complex (total inhibition constant $1.7 \times 10^{-9}$M), from which the inhibitor is only slowly disassociated. The inhibition constant of the first bonding step was lower than the $K_m$ value for the substrate adenosine ($K_m = 2 \times 10^{-5}$M), but was surprisingly comparable to the $IC_{50}$ value for the inhibition of cGMP-stimulated PDE in the present test. Consequently doses of more than $10^{-7}$M of EHNA have inhibiting effects on both enzymes.

Commercially available EHNA, which was used in the present investigation, is a racemic mixture comprising erythro-(+)-9-(2S-hydroxy-3R-nonyl)-adenine and erythro-(−)-9-(2R-hydroxy-3S-nonyl)-adenine [(±)-EHNA]. The $K_1$ value of (±)-EHNA for human ADA was measured to be 4 nM, a number that corresponds to approximately 2 times the value of (+)-(2S, 3R)-EHNA. However, much higher concentrations of EHNA were actually required to inhibit ADA in intact cells.

The cGMP-stimulated PDE is one of at least two soluble isoenzymes, which split the two second messenger molecules—cAMP and cGMP. The ability of this enzyme to hydrolyze cAMP or cGMP is increased in the presence of cGMP as a consequence of allostearic activation of the enzyme, thus becoming a receptor for cGMP. However, the exact physiological function of this enzyme is still not known. The present results suggest that cGMP-stimulated PDE is an important factor in the control of the heart rhythm.

PDE-II inhibitors like EHNA prove to be prototype drugs with inhibiting effects both on adenosine deaminase and cGMP-stimulated PDE. In contrast, 2-o-propoxyphenyl-8-azapurine-6-one is a selective PDE inhibitor that does not inhibit the adenosine deaminase.

The following examples explain the invention.

EXAMPLE 1

Tablets for oral administration

| A. Direct compression (1) | |
|---|---|
| Active agent: EHNA | 2 mg/tablet |
| magnesium stearate BP | 0.65 mg/tablet |
| water-free lactose | 80 mg/tablet |

The active agent is mixed with the anhydrous lactose and the magnesium stearate; and the mixture is sieved. The resulting mixture is compressed into tablets using a tableting machine.

The same formulation can also be done with 2-o-propoxyphenyl-8-azapurine-6-one as the active agent. An activator of guanyl cyclase may or may not be added.

| (2) | |
|---|---|
| Active agent: EHNA | 2.5 mg/tablet |
| magnesium stearate BP | 0.7 mg/tablet |
| microcrystalline cellulose NF | 100 mg/tablet |

The active agent is sieved and mixed with the microcrystalline cellulose and the magnesium stearate. The resulting mixture is is compressed into tablets using a tableting machine.

The same formulation can also be conducted with 2-o-propoxyphenyl-8-azapurine-6-one as the active agent. An activator of guanyl cyclase may or may not be added.

| B. Wet Granulation | |
|---|---|
| active agent: EHNA | 30.0 mg/tablet |
| lactose BP | 150.0 mg/tablet |
| starch BP | 30.0 mg/tablet |
| pregelatinized corn starch BP | 15.0 mg/tablet |
| magnesium stearate BP | 1.5 mg/tablet |

The active agent is sieved through a suitable screen and mixed with the lactose, the starch and the pregelatinized corn starch. A suitable volume of purified water is added; and the powder is granulated. Following drying, the granulate is sieved and mixed with the magnesium stearate, The granulate is compressed into tablets having a suitable diameter using punches.

The same formulation can also be done with 2-o-propoxyphenyl-8-azapurine-6-one as the active agent. An activator of guanyl cyclase may or may not be added.

Tablets of different composition can be manufactured by modifying the ratio of active agent to lactose or the compression weight and using suitable punches.

EXAMPLE 2

| Capsules | |
|---|---|
| active agent: EHNA | 30 mg/tablet |
| free flowing starch | 150 mg/tablet |
| magnesium stearate BP | 1 mg/tablet |

The active agent is sieved and mixed with the other components. The mixture is filled into hard gelatin capsules no. 2 using a suitable device. Other capsules can be manufactured by modifying the fill weight and, if necessary, modifying the size of the capsule to match.

The same formulation can also be conducted with 2-o-propoxyphenyl-8-azapurine-6-one as the active agent. An activator of guanyl cyclase may or may not be added.

EXAMPLE 3

Injection for intravenous administration

| active agent: EHNA | 1.5–3.0 mg/ml |
|---|---|
| sodium chloride intravenous infusion, BP, 0.9% wt./vol. | 1 ml |
| batch size | 2500 ml |

The active agent is dissolved in one aliquot of the sodium chloride intravenous infusion; the solution with the sodium chloride intravenous infusion is adjusted to the volume and the solution is thoroughly mixed. The solution is filled into clear, type 1, 10 ml glass ampoules and sealed in the head space by melting the glass under nitrogen. The ampoules are sterilized for no less than 20 minutes by heating in the autoclave at 120° C.

I claim:

1. A process for the control or prophylaxis of cardiovascular disease that is not caused by ischemia or fibrillation, said process comprising administering to a human patient requiring said control or prophylaxis an effective amount of a cGNP-stimulated phosphodiesterase (PDE II) inhibitor that is erythro-9-(2-hydroxy-3-nonyl)-adenine.

2. The process of claim 1, wherein at least one guanyl cyclase activator is also administered to the patient.

3. The process of claim 2, wherein the cGMP-stimulated phosphodiesterase inhibitor and the guanyl cyclase activator are administered simultaneously or separately to the patient, or are administered gradually over time to the patient.

4. The process of claim 1, wherein the cGMP-stimulated phosphodiesterase inhibitor is administered via an oral, intraperitoneal, intramuscular, subcutaneous, intraarticular or intravenous route.

5. The process of claim 2, wherein the cGMP-stimulated phosphodiesterase inhibitor and the activator are administered via an oral, intraperitoneal, intramuscular, subcutaneous, intraarticular or intravenous route.

6. A pharmaceutical composition for control or prophylaxis of cardiovascular disease which comprises an amount effective for inhibition of cGMP-stimulated phosphodiesterase (PDE II) of erythro-9-(2-hydroxy-3-nonyl)-adenine and a guanyl cyclase activator.

7. The pharmaceutical composition of claim 6, in the form of a tablet, dragee, capsule or solution suitable for oral or injection administration.

* * * * *